(12) United States Patent
Rahimian et al.

(10) Patent No.: US 11,577,049 B2
(45) Date of Patent: *Feb. 14, 2023

(54) SYSTEMS AND METHODS FOR 3D STEREOSCOPIC ANGIOVISION, ANGIONAVIGATION AND ANGIOTHERAPEUTICS

(71) Applicant: Voxel Rad, Ltd., Irvine, CA (US)

(72) Inventors: Javad Rahimian, Irvine, CA (US); Mohammad Shenasa, Monte Sereno, CA (US)

(73) Assignee: Voxel Rad, Ltd., Irvine, CA (US)

( * ) Notice: Subject to any disclaimer, the term of this patent is extended or adjusted under 35 U.S.C. 154(b) by 865 days.

This patent is subject to a terminal disclaimer.

(21) Appl. No.: 16/509,284

(22) Filed: Jul. 11, 2019

(65) Prior Publication Data

US 2020/0009352 A1 Jan. 9, 2020

Related U.S. Application Data

(63) Continuation of application No. 13/399,704, filed on Feb. 17, 2012, now Pat. No. 10,391,277.

(Continued)

(51) Int. Cl.
*A61B 34/20* (2016.01)
*A61B 90/00* (2016.01)
(Continued)

(52) U.S. Cl.
CPC ..... *A61M 25/0105* (2013.01); *A61B 1/00193* (2013.01); *A61B 5/062* (2013.01);
(Continued)

(58) Field of Classification Search
CPC ........ A61B 2034/101; A61B 2034/102; A61B 2034/105; A61B 2034/107;
(Continued)

(56) References Cited

U.S. PATENT DOCUMENTS 6,006,126 A * 12/1999 Cosman ............... G06V 10/245
600/417
6,083,170 A 7/2000 Ben-Haim
(Continued)

FOREIGN PATENT DOCUMENTS

WO WO 03/034705 A2 4/2003

OTHER PUBLICATIONS

Dukkipati, et al., *Pulmonary Vein Isolation Using a Visually Guided Laser Balloon Catheter: The First 200-Patient Multicenter Clinical Experience*, Circ Arrhythm Electrophysiol. 2013;6:467-142; originally published online Apr. 4, 2013.

(Continued)

*Primary Examiner* — Carolyn A Pehlke
(74) *Attorney, Agent, or Firm* — Knobbe, Martens, Olson & Bear, LLP (57) ABSTRACT

Devices, systems, and methods for catheterization through angionavigation, cardionavigation, or brain navigation to diagnose or treat diseased areas through direct imaging using tracking, such as radiofrequency, infrared, or ultrasound tracking, of the catheter through the patient's vascular anatomy. A steerable catheter with six degrees of freedom having at least a camera and fiber optic bundle, and one or more active or passive electromagnetic tracking sensors located on the catheter is guided through the vascular system under direct imaging. The direct imaging can be assisted with at least one of MRA imaging, CT angiography imaging, or 3DRA imaging as the roadmap acquired prior to or during 3D stereoangiovision. The system comprises RF transceivers to provide positioning information from the sensors, a processor executing navigation software to fuse the tracking information from the tracking sensors with the imaging roadmap, and a display to display the location of the catheter on the roadmap.

22 Claims, 9 Drawing Sheets

Related U.S. Application Data (60) Provisional application No. 61/444,665, filed on Feb. 18, 2011.

(51) Int. Cl.
| | | |
|---|---|---|
| *A61B 34/10* | (2016.01) | |
| *A61M 25/01* | (2006.01) | |
| *A61B 1/00* | (2006.01) | |
| *A61B 5/06* | (2006.01) | |
| *A61B 6/00* | (2006.01) | |
| A61B 5/055 | (2006.01) | |
| A61B 6/04 | (2006.01) | |
| A61B 18/14 | (2006.01) | |
| A61B 18/24 | (2006.01) | |
| A61B 18/00 | (2006.01) | |
| A61B 18/02 | (2006.01) | |

(52) U.S. Cl.
CPC .............. *A61B 6/481* (2013.01); *A61B 6/503* (2013.01); *A61B 6/504* (2013.01); *A61B 34/20* (2016.02); *A61B 5/055* (2013.01); *A61B 6/0407* (2013.01); *A61B 18/1492* (2013.01); *A61B 18/24* (2013.01); *A61B 2018/0022* (2013.01); *A61B 2018/00267* (2013.01); *A61B 2018/00357* (2013.01); *A61B 2018/00577* (2013.01); *A61B 2018/0212* (2013.01); *A61B 2034/105* (2016.02); *A61B 2034/107* (2016.02); *A61B 2034/2051* (2016.02); *A61B 2090/364* (2016.02); *A61B 2218/002* (2013.01); *A61M 2025/0166* (2013.01)

(58) Field of Classification Search
CPC .... A61B 2034/2046; A61B 2034/2051; A61B 2034/2055; A61B 2034/2057; A61B 2034/301; A61B 2034/303; A61B 34/20; A61B 34/10; A61B 34/25; A61B 34/30; A61B 5/055; A61B 5/06; A61B 5/061; A61B 5/062; A61B 5/064; A61B 5/066; G01R 33/5635; G01R 33/563; G01R 33/56316

See application file for complete search history.

(56) References Cited

U.S. PATENT DOCUMENTS

| | | | |
|---|---|---|---|
| 6,144,875 | A | 11/2000 | Schweikard et al. |
| 7,728,868 | B2 | 6/2010 | Razzaque et al. |
| 8,218,846 | B2 | 7/2012 | Trumer et al. |
| 8,494,246 | B2 | 7/2013 | Trumer et al. |
| 8,758,263 | B1 | 6/2014 | Rahimian et al. |
| 10,391,277 | B2 | 8/2019 | Rahimian et al. |
| 2003/0179308 | A1 | 9/2003 | Zamorano et al. |
| 2004/0097806 | A1 | 5/2004 | Hunter et al. |
| 2005/0054910 | A1 | 3/2005 | Tremblay et al. |
| 2007/0083193 | A1 | 4/2007 | Werneth et al. |
| 2008/0021297 | A1 | 1/2008 | Boosten |
| 2008/0043901 | A1 | 2/2008 | Maschke |
| 2008/0118135 | A1 | 5/2008 | Averbuch et al. |
| 2008/0171934 | A1 | 7/2008 | Greenan et al. |
| 2009/0088756 | A1 | 4/2009 | Anderson |
| 2009/0216221 | A1 | 8/2009 | Davis et al. |
| 2009/0312629 | A1 | 12/2009 | Razzaque et al. |
| 2010/0094081 | A1 | 4/2010 | Rothe et al. |
| 2010/0268067 | A1 | 10/2010 | Razzaque et al. |
| 2010/0274311 | A1 | 10/2010 | Vaidyanathan |
| 2011/0130651 | A1 | 6/2011 | Chen et al. |
| 2012/0215094 | A1 | 8/2012 | Rahimian et al. |

OTHER PUBLICATIONS

Dukkipati, et al., *The Durability of Pulmonary Vein Isolation Using the Visually Guided Laser Balloon Catheter: Multicenter Results of Pulmonary Vein Remapping Studies*, Heart Rhythm Society, pp. 919-925, 2012.

Everly S, Bahnson T, Koontz J, et al. Intracardiac acoustic radiation force: A novel imaging method for intraprocedural evaluation of radiofrequency ablation lesions. Heart Rhythm. 2012;9:1855-1862.

J. Rahimian, J.C. Chen, A.A. Rao, M.R. Girvigian, M.J. Miller, H.E. Greathouse. Geometric Accuracy of Novalis Stereotactic Radiosurgery System for Trigeminal Neuralgia Treatment. J. Neurosurgery (Suppl 3) 101: 351-355, 2004.

J. Rahimian, J.C.T. Chen, M. R. Girvigian, M.J. Miller, R. Rahimian. Frame Based and Frameless Precision of BrainLab Novalis © Stereotactic Radiosurgery System. Shaped Beam Radiosurgery, Chapter 4, A. de Salles, editor, Springer Verlag Publishers, 2011.

Metzner, et al., *One-Year Clinical Outcome After Pulmonary Vein Isolation Using the Novel Endoscopic Ablation System in Patients with Paroxysmal Atrial Fibrillation*. From the Asklepios Klinik St. Georg, Department of Cardiology, Hamburg, Germany, pp. 988-993, 2011.

Metzner, et al., *The Influence of Varying Energy Settings on Efficacy and Safety of Endoscopic Pulmonary Vein Isolation*, from the Departments of Cardiology and Internal Medicine, Asklepios Klinik St. Georg, Hamburg, Germany, pp. 1380-1385, 2012.

Miyazaki, et al., "Non-contrast-enhanced MR angiography using 3D ECG-synchronized half-Fourier fast spin echo." Journal of Magnetic Resonance Imaging, vol. 12, Issue 5, Nov. 2000, pp. 776-783.

Reddy, et al., *Visually-Guided Balloon Catheter Ablation of Atrial Fibrillation: Experimental Feasibility and First-in-Human Multicenter Clinical Outcome*, Circulation. 2009; 120:12-20; originally published online Jun. 22, 2009.

Schmidt, et al., *Feasibility of Circumferential Pulmonary Vein Isolation Using a Novel Endoscopic Ablation System*, Circ Arrhythm Electrophysiol. 2010;3:481-488; originally published online Jul. 24, 2010.

(Srinivas R. Dukkipati et al. Visual Balloon-Guided Point-by-Point Ablation: Reliable, Reproducible, an Persistent Pulmonary Vein Isolation, http://circep.ahajournals.org/content/3/3/266.full; and William W.B. Chik, et. al. In Vivo Evaluation of Virtual Electrode Mapping and Ablation Utilizing a Direct Endocardial Visualization Ablation Catheter. Journal of Cardiovascular Electrophysiology vol. 23, No. 1,pp. 88-96, Jan. 2012).

\* cited by examiner

SYSTEMS AND METHODS FOR 3D STEREOSCOPIC ANGIOVISION, ANGIONAVIGATION AND ANGIOTHERAPEUTICS

This application is a continuation of U.S. patent application Ser. No. 13/399,704 filed on Feb. 17, 2012 and entitled SYSTEMS AND METHODS FOR 3D STEREOSCOPIC ANGIOVISION, ANGIONAVIGATION AND ANGIOTHERAPEUTICS, which application claims the benefit of priority under 35 U.S.C. § 119(e) of U.S. Provisional Application No. 61/444,665 filed on Feb. 18, 2011 and entitled SYSTEMS AND METHODS FOR 3D STEREOSCOPIC ANGIOVISION, ANGIONAVIGATION AND ANGIOTHERAPEUTICS, the entireties of which are hereby incorporated herein by reference to be considered a part of this specification.

BACKGROUND

Transcatheter procedures are rapidly replacing surgical procedures, such as coronary interventions for coronary artery bypass grafting (CABG), intravascular repair and stenting for vascular surgery, and catheter ablation of complex arrhythmias for arrhythmia surgery. Typically transcatheter approaches are done under fluoroscopy which uses ionizing radiation. Radiation exposure is of concern to the public and medical community. Medical imaging is a significant cause of manmade radiation exposure, hence many guidelines and appropriateness use of this procedure and imaging technology has been developed.

Medical treatment of patients with cardiovascular disease such as atherosclerosis, cardiac arrhythmias, aneurysms, often includes a medical professional performing angiography. Angiography comprises obtaining x-ray fluoroscopic imaging that involves guiding a catheter through femoral or carotid arteries (brain vascular interventions) with x-ray fluoroscopic image guidance, and frequent injection of iodinated contrast agent to visualize internal anatomy of the vasculature to evaluate blood flow, constrictions, or blockage, and plan an appropriate treatment. Traditional systems and methods for angiography can expose the patient, the angiography suite staff, and the physicians to significant doses of ionizing radiation.

X-ray angiography is considered the industry's typical imaging standard for the evaluation of cardiovascular anatomy within the body. The angiography procedure requires insertion of a catheter with guide wires through an artery or vein with frequent injection of contrast media, and use of x-ray fluoroscopy to guide the catheter to the area of interest. The x-ray angiography provides high resolution imaging showing vasculature anatomical details, left ventricular ejection fraction, and cardiac output. However, x-ray angiography still requires fluoroscopy, and can expose the patient, the angiography suite staff, and the physicians to significant doses of ionizing radiation.

Other methods, such as magnetic resonance angiography (MRA), computed tomography angiography (CTA), and 3D rotational angiography (3DRA) with contrast medium, are used to delineate the cardio-vascular system. While MRA has the advantage of using non-ionizing radio frequency (RF) energy, it does not provide by itself real-time guidance within the vasculature. CTA and 3DRA use ionizing radiation and an iodinated contrast agent, which again can expose the patient, the angiography suite staff, and the physicians to significant doses of ionizing radiation.

These methods have the risk of exposing patients and hospital personnel to ionizing radiation. The risk is substantial. There are risks of skin erythema, skin necrosis, malignancy, genetic abnormalities, and adverse reactions to iodinated contrast media including kidney shut down and death. Further, from the interventional cardiologist's perspective, fluoroscopy systems can also be problematic because the system is bulky and limits intra operative flexibility as well as free movement of angiography instruments.

Atrial fibrillation (AF) is the most common sustained arrhythmia of many etiologies. According to reports, there are about six to seven million Americans suffering from AF and it is predicted that by 2050 AF prevalence may reach 15 to 16 million. Approximately 35% of hospitalizations due to arrhythmias are from AF. AF costs Medicare more than 15.7 billion dollars annually.

Stroke is one of the most significant and devastating burdens of AF. Stroke affects 800,000 Americans annually—almost one every forty seconds. Stroke is the third leading cause of death and the number one cause of disability. Eighty-seven percent of strokes are ischemic, i.e., embolic, and the most common source is related by far by AF.

Anti-arrhythmic drugs are used in 90% of cases. However the success rate of these medications is less than 50%. More recent trials revealed negative outcomes of anti-arrhythmic therapy. Two of the most recent trials were prematurely terminated due to adverse effects of these drugs (Pallas; N Engl J Med 2011; 365:2268-2276, and Alphee trial; Kowey P R. Circulation; 2011; doi: 10. 1161/CIRCULATIONAHA. 111.072561).

Transcatheter ablation of AF is increasingly used to "cure the arrhythmia". The procedure typically requires multiple catheter insertions and the use of radio frequency currents. High intensity focused ultrasound or cryoablation using a balloon are alternates having less success. The success rate of paroxysmal AF ablation with low co-morbidity is about 70-80%. In patients with advanced heart disease such as heart failure and persistent AF, the acute success rate of AF ablation is about 50-60% with a high recurrence rate at one year.

AF ablation using RF typically requires multiple site burns and is typically a lengthy procedure with high radiation exposure. A main reason for the low success rate is the anatomical complexity of the arrhythmogenic substrate and reconnection of isolated pulmonary veins to the left atrium. AF is an evolving disease and a moving target by itself. Successful AF ablation can depend on completely ablating target tissue without any gaps. The gaps are usually the cause of reconnection and recurrence of AF.

Ventricular tachyarrhythmias (VT) are another arrhythmia that often causes syncope (loss of consciousness) and cardiac arrest. It is estimated that about 350,000 to 450,000 cases of sudden cardiac deaths occur annually in the U.S. The majority of these cases are due to VT and ventricular fibrillation. So far the only effective method to abort and or prevent sudden cardiac death is implantation of cardioverter defibrillator devices known as ICD's. This procedure is costly and designed to terminate arrhythmias when it occurs. It does not however prevent nor cure as it does not eliminate or modify the arrhythmogenic substrate.

Traditional ablation catheters and electrodes have been used for transcatheter ablation of endocardial and/or epicardial arrhythmogenic tissue to treat VT. Traditional ablation catheters in these areas of the heart have limited success and a high recurrence rate. The possible cause of this is related to the complexity of the arrhythmogenic substrate and the mechanism of arrhythmia itself. Traditional ablation catheters and electrodes do not identify the characteristics of the arrhythmogenic substrate via direct visualization and monitoring while ablating, nor do they ablate uniformly without possible gaps.

SUMMARY

In certain embodiments, systems and methods for a universal angiovision technique are disclosed. The universal angiovision technique is minimally invasive with high precision and can be used in most anatomic sites to image or intervene, such as stent placement, ventricular shunt evaluations, image guided cytotoxic drug delivery into tumors through their afferent arteries or radioactive seed implants directly into tumors. Further, the technique can be used in radiofrequency or laser ablation of tumors such as hepatomas, and cryogenic treatment of tumors such as prostate tumors. In an embodiment, the technique permits image guided intervention in the heart, such as RF or laser ablation of arrhythmogenic regions, and angioplasty in many areas of the body. The organs that angionavigation can be used to treat or image, include, but are not limited to, the liver, lungs, kidneys, pelvis, pancreas, pleura, brain, esophagus, stomach, small bowl, colon and rectum. In an embodiment, the technique does not use ionizing radiation for imaging or interventions.

In an embodiment, angionavigation and angiovision techniques provide many advantages over x-ray angiography systems. The extent of the arterial plaques and the blood flow are directly visible to the physician, and does not have to be inferred from iodinated contrast agent flow studies under a fluoroscope. Without the contrast agent blocked arteries can look normal, while direct visualization or infrared technology can identify the type of plaques with or without calcifications. The technique can be faster as there is no need for the staff to clear the room to take x-rays and inject the patient with contrast agent. This may make anesthesia time significantly shorter for an angionavigation system.

Systems and methods of transcatheter imaging and intervention are described that require reduced, minimal, or no radiation exposure. Furthermore, techniques that precisely identify target sites for intervention of complex intravascular and intra-cardiac therapeutics are disclosed.

An embodiment relates to devices and methods for angioendoscopy of cardiovascular systems and therapeutic intervention. In particular, an embodiment relates to devices and methods for catheterization through angioendoscopy of heart or brain to diagnose or treat diseased areas through direct imaging, and radiofrequency or infrared tracking of the catheter through the patient's vascular and cardiac anatomy.

An embodiment discloses a steerable catheter having 6 degrees of freedom with a complimentary metal-oxide semiconductor (CMOS) or charged coupled device (CCD) camera, preferably operatively connected to at least one 10K pixel fiber optics bundle, and at least one active or passive sensor embedded in the catheter. The sensors communicate with an Electromagnetic Tracking System (EMTS). The catheter is guided through the vascular system by direct imaging assisted with, for example, magnetic resonance angiography (MRA), acquired prior to angioscopy. In other embodiments, if MRA is not available or if the patient is claustrophobic, or allergic to Gadolinium injection, the catheter is guided through the vascular system by direct imaging assisted with, for example, computed tomography angiography (CTA), or 3D rotational angiography (3DRA) imaging acquired prior to angioscopy. The CTA and 3DRA ionizing radiation dose is significantly less than conventional angiography.

Another embodiment discloses an ablation catheter that is integrated with the angiovision catheter to uniformly or non-uniformly generate heat or cryoablation of the arrhythmogenic substrate. A multi-strut electrode on the ablation catheter may be made of Nitinol alloy with predefined geometric 3D shape memory that can be opened after insertion intra-arterially or intravenously into the atrium to ablate selectively the arrhythmogenic tissues under direct 3D stereovision. In an embodiment, the ablation catheter rotates ablating a three-dimensional area. The uniform ablation reduces gaps in the ablation which are often the cause of reconnection and recurrence of AF and other cardiac arrhythmias.

Certain embodiments relate to a method of navigation within body structures utilizing non-ionizing and non-iodinated agents. The method comprises loading a digital image of a patient into a memory storage device. The digital image is acquired without using ionizing and iodating agents and the digital image includes images of at least one IR marker placed on the patient prior to acquiring the digital image. The method further comprises generating stereotactic coordinates in a stereotactic coordinate system based at least in part on the location of the at least one IR marker and an entry point of a catheter. The catheter includes at least one electromagnetic sensor associated with an electromagnet coordinate system. The method further comprises generating a rendering of the patient's anatomical structure, where the rendering includes an indication of the entry point and at least one target, generating a roadmap from the entry point to the target, co-registering the electromagnetic and the stereotactic coordinate systems, obtaining positional information from sensors, and displaying the rendering including indications for a position of catheter, target, entry point, and roadmap.

According to a number of embodiments, the disclosure relates to a system for navigating within body structures utilizing non-ionizing and non-iodinated agents. The system comprises computer hardware including at least one computer processor, and computer-readable storage including computer-readable instructions that, when executed by the computer processor, cause the computer hardware to perform operations defined by the computer-executable instructions. The computer-readable instructions include loading a digital image of a patient into a memory storage device. The digital image is acquired without using ionizing and iodinated contrast agents and the digital image includes images of at least one IR marker placed on the patient prior to acquiring the digital image. The method further comprises generating stereotactic coordinates in a stereotactic coordinate system based at least in part on the location of the at least one IR marker and an entry point of a catheter. The catheter includes at least one electromagnetic sensor associated with an electromagnet coordinate system. The method further comprises generating a rendering of the patient's anatomical structure, where the rendering includes an indication of the entry point and at least one target, generating a roadmap from the entry point to the target, co-registering the electromagnetic and the stereotactic coordinate systems, obtaining positional information from sensors, and displaying the rendering including indications for a position of catheter, target, entry point, and roadmap. A main advantage of some embodiments of an angionavigation system over the currently approved or investigational devices is that it can be completely ionizing radiation free.

For purposes of summarizing the invention, certain aspects, advantages, and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

DETAILED DESCRIPTION OF THE PREFERRED EMBODIMENT

A general architecture that implements the various features of the invention will now be described with reference to the drawings. The drawings and the associated descriptions are provided to illustrate embodiments of the invention and not to limit the scope of the invention.

As used herein, the terms proximal and distal refer to a direction or a position along a longitudinal axis of a catheter or medical instrument. Proximal refers to the end of the catheter or medical instrument closer to the operator, while distal refers to the end of the catheter or medical instrument closer to the patient. For example, a first point is proximal to a second point if it is closer to the operator end of the catheter or medical instrument than the second point. The term "anatomically proximal" means closer to the heart and more specifically to the aortic valve while "anatomically distal" is further from the aortic valve. The measurement term French, abbreviated Fr or F, is defined as three times the diameter of a device as measured in mm. Thus, a 3 mm diameter catheter is 9 French in diameter.

Today, physicians are using minimally invasive medical/surgical procedures that are less traumatic and more cost-effective. Most of these newer procedures incorporate small or micropuncture catheters hollow flexible tubes that physicians insert in small incisions in a major artery, such as the femoral artery in the thigh. The physician inserts the catheter through the arterial or venous network to the target area. Millimeter-size tools can then be guided through the tube to fix the medical condition. A key advantage of this technique is that patients recover in days, not weeks. For example, balloon angioplasty (in which a small balloon is inserted through the catheter and, once at the end, inflated to open up a blocked artery) is now routinely conducted on an outpatient basis.

Certain embodiments relate to systems and methods for performing an image-guided angioendoscopy using MRA or CTA imaging, 3DRA, and a steerable catheter system. The steerable catheter system comprises a steerable catheter having six degrees of freedom (6D), a CMOS or CCD camera and associated high resolution fiber optics bundle, and tracking sensors. The steerable catheter system further comprises at least one CCD camera and an RF Global Positioning System (GPS) guidance system utilizing the Electromagnetic Tracking System Principles (EMTS). Two infrared cameras are installed in the ceiling to read the stereotactic fiduciary infrared markers placed on the patient. The system preferably can visually image and inspect the internal structure of arteries, veins, and endocardium or epicardium similar to an endoscopic procedure. The system further measures blood flow without a need for x-ray fluoroscopy and iodinated contrast agent with a high degree of accuracy. This advantageously has minimal patient and hospital personnel adverse effects from ionizing radiation used in other imaging systems.

A planning MR angiography scan is acquired prior to angionavigation with stereotactic fiduciary markers to produce digitally reconstructed 3D rendering of vascular system. At least one RF tracking sensor embedded in strategic locations in the catheter sends RF signals at a frequency having a rate of approximately 40 Hz to approximately 50 Hz. In an embodiment, three RF tracking sensors are embedded in the catheter. The signals are detected by the in-room GPS system comprising radio receivers positioned inside the angionavigation room. The GPS system detects each individual signal, computes the position of each sensor, and maps their locations using six degrees of freedom (6D) on the planning MRA 3D rendered image or roadmap. In addition, the 3D video images captured via the fiber optic bundle and camera are co-registered or fused and displayed with the MRA 3D rendered image data set in real time identifying the target. A monitor, such as a high definition monitor, displays the resulting 3D image.

The catheter is guided in the vascular system using the 6D steerable capabilities. A plurality of measurements, therapies and interventions can be performed using the image-guided catheter and system. A laser light is transmitted through the fiber optics bundle with short pulses to measure the blood flow at different regions before, and after angioplasty or other interventions using laser Doppler principles. Similarly an ultrasonic transducer can measure blood flow, blood pressure, and volume. A stenotic region of an artery can be identified using the 3D stereoangiovision and be marked on the MRA. An angioplasty balloon may be inserted to the same position to perform the angioplasty procedure, and place a stent under direct angioendoscopic visualization, or other interventions as needed.

In certain embodiments, a system for performing angiovision and angionavigation imaging based on principles of 3D stereoscopic imaging is disclosed. There is a growing appreciation that two-dimensional projections of 3D scenes, traditionally referred to as "3D computer graphics", can be insufficient for inspection, navigation, and comprehension of some types of multivariate data. Without the benefit of 3D rendering, even high quality images that have excellent perspective depictions still appear unrealistic and flat. For such application environments, the human depth cues of stereopsis, motion parallax, and (perhaps to a lesser extent) ocular accommodations are increasingly recognized as significant and important for facilitating image understanding and realism.

Therefore, in an embodiment, one, two or more fiber optic bundles in the catheter are each connected to a CMOS camera which takes pictures and transmits to an image processing computer system. The computer image processor makes the 3D stereoscopic images with depth perception possible that can be displayed on 3D display monitor for the interventional physician. The technique is extremely valuable in detection, and evaluation of abnormalities such as plaques, size, and definitions of tumors, monitoring treatments such as ablation of arrhythmogenic pulmonary vein antrum, and the like. In addition, 3D stereoscopic visualization has significant impact in diagnosing, treating, staging, and managing digestive system abnormalities including tumors, ulcers, of esophagus, stomach, small intestine, colon, rectum, and the like.

Figure 1:
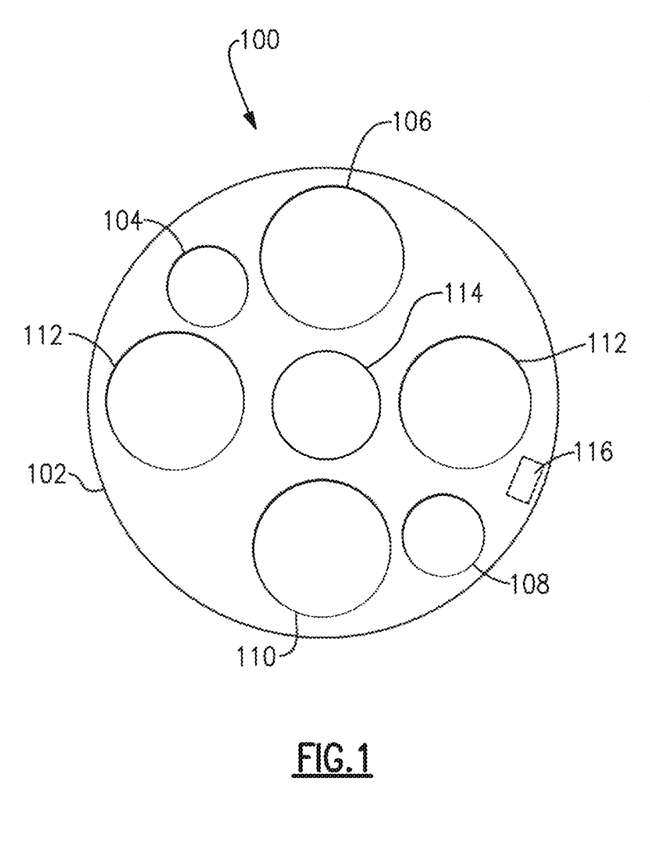
FIG. 1 is a cross-sectional view of an angionavigation catheter, according to an embodiment.

For a more detailed understanding of the invention, reference is first made to FIG. 1. FIG. 1 is a cross-sectional view of an angionavigation catheter 100, according to an embodiment. The catheter 100 along with a guidance system can be used for improved direct vascular visualization, stent delivery, and other therapeutic interventions without the use of x-ray fluoroscopy.

The angionavigation catheter 100 comprises axially elongate tubing 102 including a plurality of lumen. In an embodiment, the outer diameter of the catheter tubing 102 is between approximately 3 mm to approximately 7 mm. In another embodiment, the outer diameter of the catheter tubing 102 is preferably between approximately 4 mm to approximately 6 mm, and more preferably is approximately 5 mm or 15 Fr. In other embodiments the diameter is greater than approximately 7 mm. In further embodiments, the diameter is less than approximately 3 mm.

The catheter 100 can further comprise at least one of an ultrasound transducer 104, electrograms and pacing sensors 106, an irrigation tube 108, at least one high intensity light source 110, at least one fiber optic bundle 112 operable attached to a camera, and an ablation catheter 114. Each component 104, 106, 108, 110 112, 114 is inserted through an appropriately sized lumen of the plurality of lumen within the tubing 102, respectively, as is known to one of skill in the art in light of this disclosure. The catheter 100 further comprises at least one tracking sensor 116. Further yet, the catheter 100 comprises at least one guidewire to control the movement of the catheter 100 through the patient's body as is known to one of skill in the art in light of this disclosure. In an embodiment, the catheter utilizes the at least one guidewire to move the catheter with 6 degrees of freedom (forward/backward, up/down, left/right, pitch, roll, and yaw). Components 104, 106, 108, 110 112, 114 can be added or removed as necessary. For example, when the catheter 100 is in place, the operator can remove the guidewire and insert the ultrasound transducer 104 to measure blood flow, the diameter of the arteries, or the like.

In another embodiment, the catheter 100 may not require a guidewire for rigidity but can accommodate one if necessary for positioning.

The ultrasound transducer 104 comprises a miniaturized ultrasound transducer to measure blood flow, volume, and pressure and characterize arterial plaques. The ultrasound transducer 104 can measure a combination of pressure and volume (P-V). The electrograms and pacing sensors 106 measure and pace cardiac electrical activity, as is known to one of skill in the art in light of this disclosure. In an embodiment, the catheter 100 combines pressure sensors 104 and electrodes 106 for simultaneous high fidelity pressure and volume measurements, enabling minimally invasive, continuous, intra-cardiac pressure-volume analysis. In other embodiments, the catheter 100 comprises cryoballoons, laserballoon, RF, high intensity ultrasound, contact force sensing, and basket electrodes.

In other embodiments, the catheter 100 uses other sensors to acquire patient information. For example, a condition sensing tag with circuitry may be embedded in the catheter 100 to detect the blood flow, blood chemistry, pressure, volume, monitor its environmental condition, and send back the information continuously to a computer system. In some embodiments, sensors are built into the tip of the catheters 100 to sense pH, motion, pressure, volume, or other parameters.

The irrigation tube 108 provides irrigation fluid to irrigate the catheter tip, including the camera. The high intensity light source 110 provides high intensity light to illuminate the camera's field of view. In an embodiment, the high intensity light source 110 is a krypton light source, such as an S3 Krypton series Laser Light by WickedLaser.com, a LED high intensity light source, such as Stryker L9000 or X8000 LED light sources by Stryker.com, and the like.

In an embodiment, the fiber optic bundle 112 comprises two high resolution fiber optic bundles of approximately 10,000 pixels each, such as for example, Fujikura Quartz Fiber Bundle 10K or 15K pixels by Fujikura.com, and the like. Each fiber optic bundle attaches to a high resolution camera, such as a CMOS USB2 camera, and the like. An example of a high resolution camera is an S-Series Ultra-Compact USB2,0 Color 3MP camera by mightexsystems.com. The camera takes pictures and transmits to an image processing computer system for display.

The ablation catheter 114 is deployed through the angionavigation catheter 100 to ablate arrhythmogenic substrate by heat or cryotherapy. In an embodiment, the ablation catheter 114 is a commercially available ablation catheter, such as a Medtronic 5F Marinr® series of RF catheter, and the like.

In another embodiment, the ablation catheter 114 a multi-strut ablation catheter 114 including a radio frequency (RF) generator which is integrated with an embodiment of the catheter 100, allowing the physician to see the tissue while ablating.

In another embodiment, the ablation catheter 114 comprises laser energy delivered via fiber optics with a 45° mirror at the tip of the ablation catheter 114 to project the energy at 90° relative to the fiber optic bundle into the arrhythmogenic tissues. In an embodiment, the fiber optic bundle comprises at least 36 optical fibers. In another embodiment, the fiber optic bundle comprises more or less than 36 optical fibers. In another embodiment, a single optical fiber carries the laser energy and projects the laser energy onto a computer controlled rotating 45-degrees mirror. The rotating mirror projects the laser energy onto the arrhythmogenic tissue in order to ablate the tissue. For example, the laser energy delivery system of the laser energy ablation catheter 114 is encased in a balloon and delivered via the angionavigation catheter 100 at the pulmonary vein antrum. The laser energy ablation catheter 114 is integrated into the angionavigation catheter 100 to allow the physician to see the tissue while ablating.

The tracking sensors 116 can be active or passive devices, such as, for example, RF transmitters, RF ID devices, RF transponders, and the like. Examples are Northern Digital Inc. (NDI) Aurora Mini 6DOF Sensor part no. 610029, NDI Aurora Micro 6DOF sensor Tool part no. 610059, and the like. The tracking sensors 116 receive from or transmit to RF receivers, RF transceivers, RF transmitter-receivers, or the like. The RF receivers/transceivers/transmitter-receivers determine the position of the sensor 116 in the vasculature using Electromagnetic Tracking System Principals (EMTS). Preferably, each tracking sensor 116 emits RF pulses at a different frequency. In an embodiment, the tracking sensors 116 transmit RF pulses between approximately 40 Hz to approximately 50 Hz. In other embodiments, the tracking sensors 116 transmit RF pulses below approximately 40 Hz or above approximately 50 Hz. In an embodiment, several in-room RF receivers/transceivers/transmitter-receivers detect the pulses, preferably continuously, and transmit the positional information to a computer system. The computer system computes the position of each RF markers, preferably in real-time, through triangulation. Further, navigational software fuses the positional information with an image of the patient, such as a planning MRA 3D rendered image. A monitor displays the resulting fused image and a surgeon viewing the fused image guides the catheter 100.

In an embodiment, the location of the catheter 100 is known within approximately 1 mm to approximately 10 mm, preferably within approximately 1 mm to approximately 5 mm, and more preferably within approximately 1 mm to approximately 2 mm. In an embodiment, the location of the catheter 100 is known within approximately 1 degree to approximately 10 degrees, preferably within approximately 1 degree to approximately 5 degrees, and more preferably within approximately 1 degree.

Figure 2A:
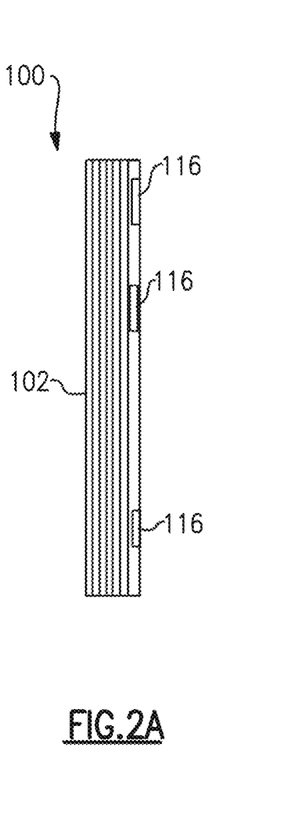
FIG. 2A is a view along the longitudinal axis of an angionavigation catheter, according to certain embodiments.

FIG. 2A is a longitudinal view a portion of the angionavigation catheter 100, according to certain embodiments. In an embodiment, the catheter 100 comprises more than one tracking sensor 116. In the illustrated embodiment, the catheter 100 comprises three tracking sensors 116. Preferably, the tracking sensors 116 are embedded in the catheter 100 at the catheter tip, approximately 10 mm from the tip, and approximately 50 mm from the tip. In other embodiments, the catheter 100 comprises less than 3 or more than 3 tracking sensors 116 and the tracking sensors 116 are located at varying distances along the catheter tubing 102. In an embodiment, the catheter tube 102 is approximately 1,000 mm long. In other embodiment, the tube length is less than or greater than approximately 1,000 mm.

Figure 3:
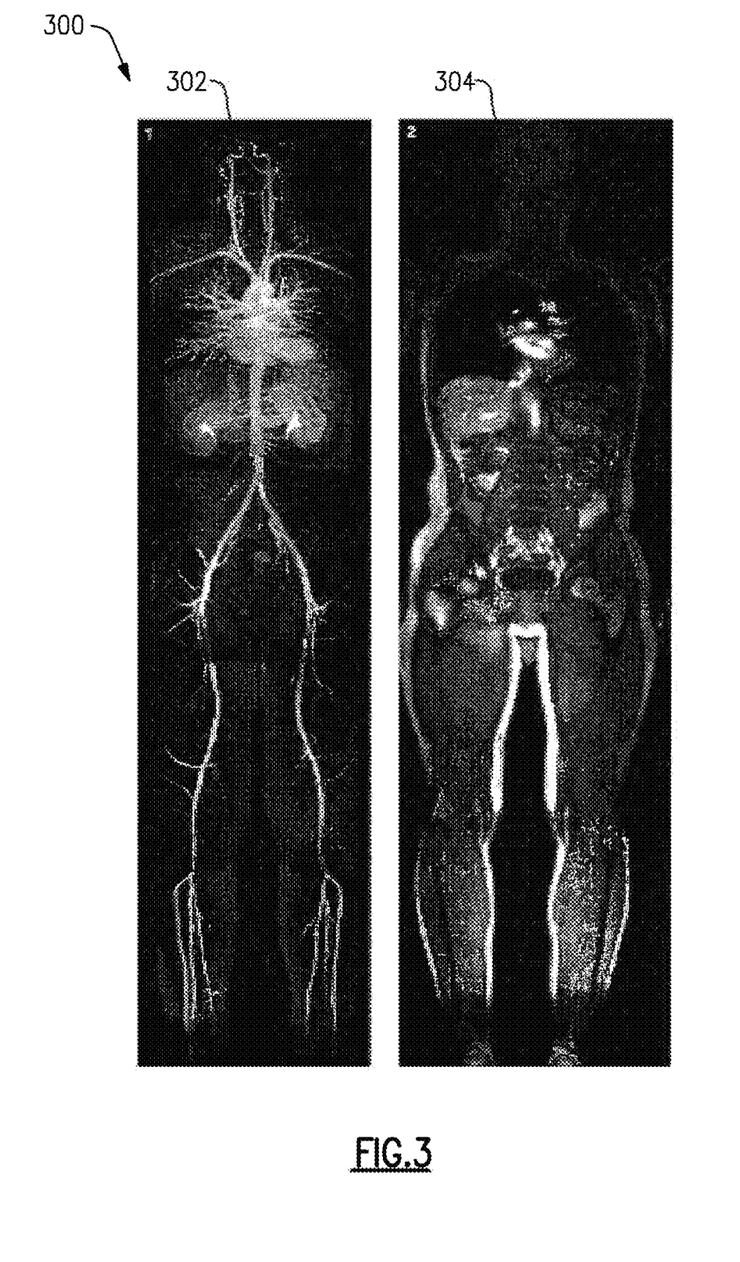
FIG. 3 is an exemplary roadmap used with an embodiment of an angionavigation catheter, according to certain embodiments.

FIG. 3 is an example of a contrast-enhanced MR angiography (CEMRA) 300 showing images 302, 304 of a body vascular system. In other embodiments, other body images, such as for example, MRA, CTA, 3DRA imaging, and the like, are taken. The image 302, 304 becomes a roadmap for direct visualization with the angionavigation catheter 100. Navigation software plots the location of the catheter 100 on the roadmap 300 using the positional information from the sensors 116.

In an embodiment, patients can obtain their pre-procedure MRA or other roadmap image prior to admission. When the patient obtains the MRA or other roadmap image prior to surgery, the room used for the surgery and the direct visualization with the catheter 100 can be a room without an x-ray angiographic system, and thus, no damaging ionizing radiation. Without an x-ray angiographic system in the room, the surgeon has greater surgical flexibility than the current system in use. In other embodiments, the roadmap imaging occurs at the same time as the use of the catheter 100.

Figure 4:
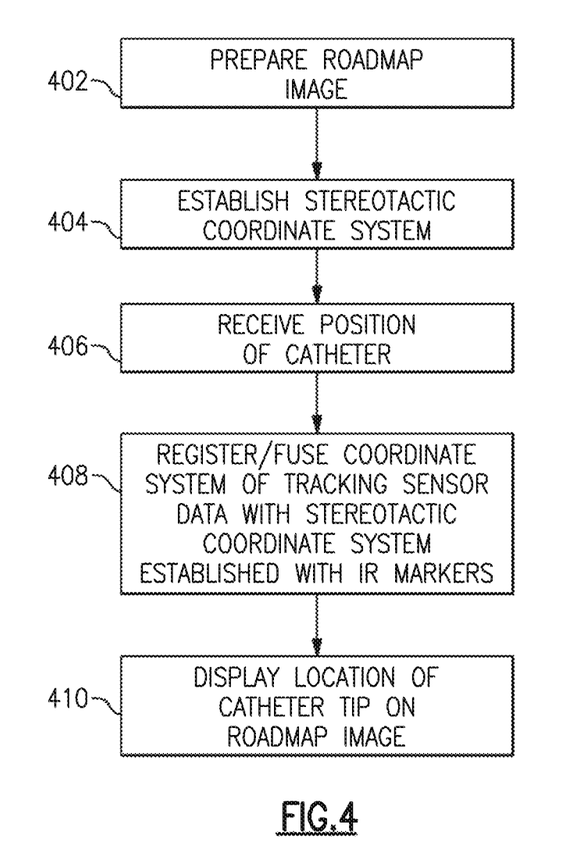
FIG. 4 is an exemplary flow chart of navigation software used to locate the position of the angionavigation catheter on the roadmap, according to certain embodiments.

FIG. 4 is an exemplary flow chart of navigation software 400 used to display the location of tip of the angionavigation catheter 100 on the roadmap 300. An embodiment provides image guidance by fusing the roadmap MRA or CTA images, for example, with the EMTS positioning stereotactic coordinate information to display the tip of the angionavigation catheter 100 on the roadmap. An interventional physician, for example, guides the catheter 100 using the roadmap displayed on the monitor along with the optical image of the internal structure. In an embodiment, the software will display a step by step navigation of the body's circulatory system, similar to the way a GPS displays navigational information to the driver of a car. In an embodiment, the guidance system can be programmed to be operated by a computer or a robot under the supervision of a physician.

Beginning at block 402, the process 400 optionally prepares volume rendered 3D images of the MRA acquired prior to surgery. Block 402, in an embodiment, can be software purchased from an outside source, such as Vital Images, BrainLab AG, or the like. In an embodiment, the process 400 uses the volume rendered 3D image of the patient's MRA as the roadmap image 300. In another embodiment, the process 400 does not prepare the volume rendered 3D images of the MRA and uses the MRA or other image acquired prior to the angionavigation procedure as the roadmap image 300.

At block 404, the process 400 establishes a stereotactic coordinate system. The patient's MRA image is taken with external infrared markers on the patient skin. The external infrared markers create registration locations on the stereotactic coordinate system, the origin of which is defined as the point of entry of the catheter 100. In other embodiments, the origin can be defined at other points on the patient's body. In an embodiment, an origin is defined in the Cartesian coordinate system of the stereotactic space generated by localization of the infrared markers using commercial available software, such as software from BrainLab AG.

The origin is defined as (0,0,0,0,0,0) representing the longitudinal, lateral, anterior-posterior, pitch, roll, and yaw location of the 6D steerable catheter 100. The tip of the catheter as is entered into, for example, the left femoral artery, before being snaked in will be manually marked on the navigation software 400 to merge the tip of the catheter position as a function of the stereotactic space coordinate system. As the catheter 100 is snaked into the patient, the 6D coordinates of the catheter tip will be non-zero as the catheter 100 moves away from the origin.

At block 406, the process 400 receives the position of the catheter tip. The tracking sensors 116 send signals to in-room RF receivers, which in an embodiment, triangulate the signals. The in-room RF receivers send the positional coordinate information of the catheter tip which is independent of the stereotactic coordinate system established by the infrared markers during the MRA.

At block 408, the process 400 registers or fuses the two coordinate systems by setting the origin of the coordinate system used by the RF receivers to the origin of the stereotactic coordinate system established by the infrared markers. The transmitted positional information of the catheter tip will be merged with the stereotactic space.

At block 410, the process 400 displays the location of the catheter tip on the roadmap image 300. In an embodiment, the process 400 displays on the MRA road map 300 an icon representing the catheter tip moving inside the patient. In an embodiment, the target can be located preferably within approximately 1 mm to approximately 2 mm, and within approximately 1 degree.

Figure 5:
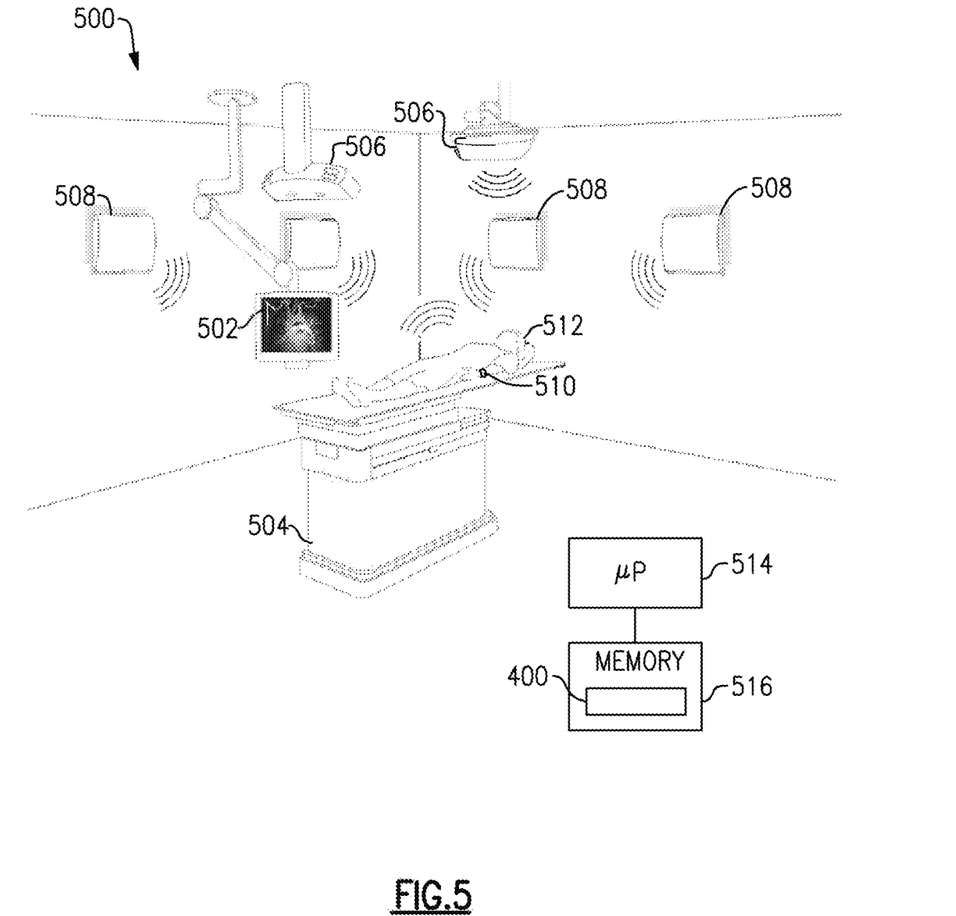
FIG. 5 illustrates an angionavigation suite, according to certain embodiments.

FIG. 5 illustrates an angionavigation suite 500, according to certain embodiments. An angionavigation system comprises the angionavigation catheter 100 including the tracking sensors 116 and the angionavigation room 500 to enable the disclosed methodologies. In an embodiment, the system can be used without use of an x-ray fluoroscopy system. FIG. 5 shows one embodiment of the angionavigation suite 500 including a monitor 502, patient couch system 504, IR cameras 506 associated with at least one stereotactic fiduciary marker 510 placed on a patient 512, RF receivers 508, and a host computer 514.

Manufacturers of medical display monitors 502 are NEC and the like. An example of the patient couch system 504 is a Couch by Medical Intelligence, a subsidiary of Elekta. Examples of the IR camera 506 and associated stereotactic markers 510 are Polaris Spectra and Polaris Vicra IR Cameras and IR Fiduciary Markers by NDI Digital, respectively.

In an embodiment, the RF receivers 508 comprise RF receivers, RF transceivers, RF transmitter-receivers, or the like. The receivers 508 receive the positional data from tracking sensors 116, determine the position of the sensors 116, and interface with the computer 514. In another embodiment, the receivers 508 comprise a tracking system, such as an electromagnetic tracking system.

An example of a tracking system is NDI's Aurora EM Tracking System including a field generator, sensors such as tracking sensors 116, at least one sensor interface units, and a system control unit. The field generator, NDI part nos. Planar FG or Table Top FG, emits a low intensity varying electromagnetic field. The varying electromagnetic field of the field generator induces small currents in the sensors 116. Sensor interface units, NDI part no. SIU, receive, amplify, and digitize the electrical signals from the sensors 116. The system control unit, NDI part no. SCU, collects information from the sensor interface units, calculates the position and orientation of each sensor 116, and interfaces with the host computer 514.

The computer 514 is associated with memory 516 which includes the navigational modules 400. The computer also interfaces with the monitor 502. The computer 514 receives the positional information from the receivers 508 and fuses the position of the catheter tip onto the roadmap image 300 for display on the monitor 502. The computer 514 and memory 516 can be located within the suite 500 or outside the suite 500.

The patient 512 is positioned on the movable robotic couch 504 in preparation for imaging, and intervention. The technique includes using an imaging procedure, such as, for example, MRA imaging, to visualize the vasculature system in the roadmap image 300, prior to or during the angionavigation. In one example procedure, a stenotic or narrowed vessel is visualized and identified as a target. The stenotic area is identified in the planning scan or roadmap image 300 with stereotactic fiduciary markers 510. The catheter 100 is inserted into and guided through the patient's vasculature. The catheter 100 is steerable in six degrees of freedom (longitudinal, lateral, anterior-posterior, pitch, roll, and yaw). Internal images are taken by the CMOS camera-fiber optic bundle 112 and fused with digitally reconstructed images of the planning scan 300. At any time, the EMTS sensor 116 embedded in the catheter 100 is interrogated with the in-room installed receivers 508 to obtain the six degrees of freedom positional information of the catheter tip, which is mapped onto the digitally reconstructed images of the planning scan 300. The IR cameras 506 and the fiduciary markers 510 provide registration information for the images.

Figure 6:
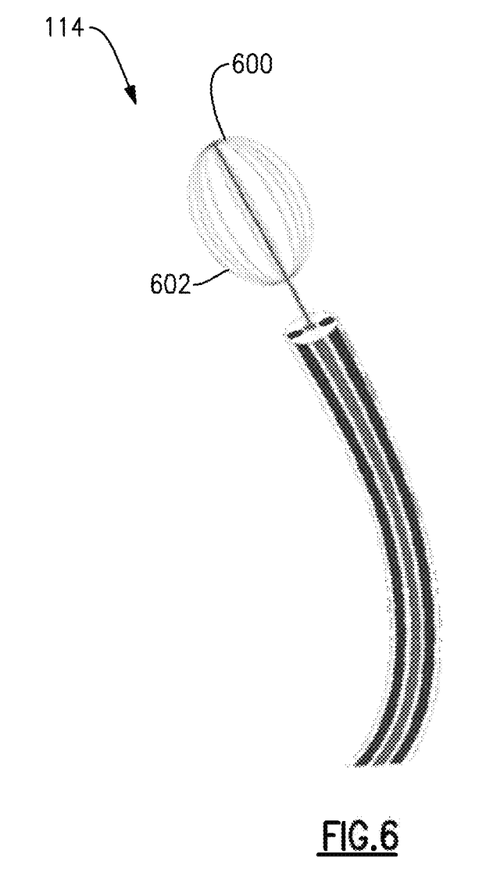
FIG. 6 illustrates a multi-strut ablation catheter, according to certain embodiments.

FIG. 6 illustrates a multi-strut ablation catheter electrode 600 of the ablation catheter 114, according to certain embodiments. The catheter electrode 600 comprises a plurality of spherical or elliptical struts 602 formed around a central hub. The number of struts depends, at least in part, on the size of the patient's pulmonary vein antrum. In an embodiment, the catheter 114 comprises 8 to 16 struts 602. In other embodiment, the catheter 114 comprises more than 16 or less than 8 struts 602. The struts 602 may be made of a Nitinol alloy, such as with predefined geometric 3D shape memory that can be opened after insertion intra arterially into the left atrium, and ablate arrhythmogenic areas.

In an embodiment, the catheter 114 is sent in the region of the heart causing arrhythmia to ablate the region. The angionavigation catheter 100 is steered to the arrhythmogenic tissue and the ablation catheter 114 may be inserted into the central lumen of the angionavigation catheter 100 to ablate. The struts 602 are operably connected to an RF generator, such as for example, Boston Scientific RF 3000, or the like, through a single wire. Ablation systems delivering RF energy are known to one of skill in the art.

In an embodiment, the ablation catheter 114 ablates multiple linear positions simultaneously. In another embodiment, the catheter 114 rotates to deliver the ablation energy to a 3 dimensional concave area. The ablation system can be programmed such that the catheter 114 treats partially or generates non-uniform heat distribution for various applications as needed or indicated for the patient. The catheter 114 can also ablate uniformly or non-uniformly as needed by cryotherapy as an alternative to heat. In a further embodiment, the catheter 600 can be used to deliver an afterloading radioactive source such as $^{32}P$ or $^{192}Ir$ radioisotopes to ablate using ionizing radiation instead of heat or cryotherapy.

Figure 7:
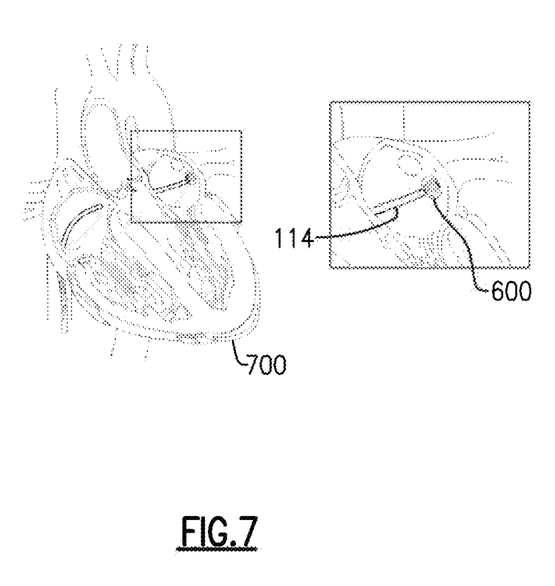
FIG. 7 illustrates an ablation catheter including an ablation electrode ablating heart tissue positioned into the pulmonary vein antrum, according to certain embodiments.

FIG. 7 illustrates the ablation catheter 114 including an embodiment of the ablation electrode 600 ablating heart tissue 700. In an embodiment, an ablation method comprises navigating the angionavigation catheter 100 to the location of the tissue to be ablated using the display monitor 502 displaying the icon representing the catheter tip on the roadmap image 300, as described above. The ablation catheter 114 is deployed from one of the lumen in the catheter 100. RF energy is applied to the catheter electrode 600 to ablate the tissue.

Figure 8A:
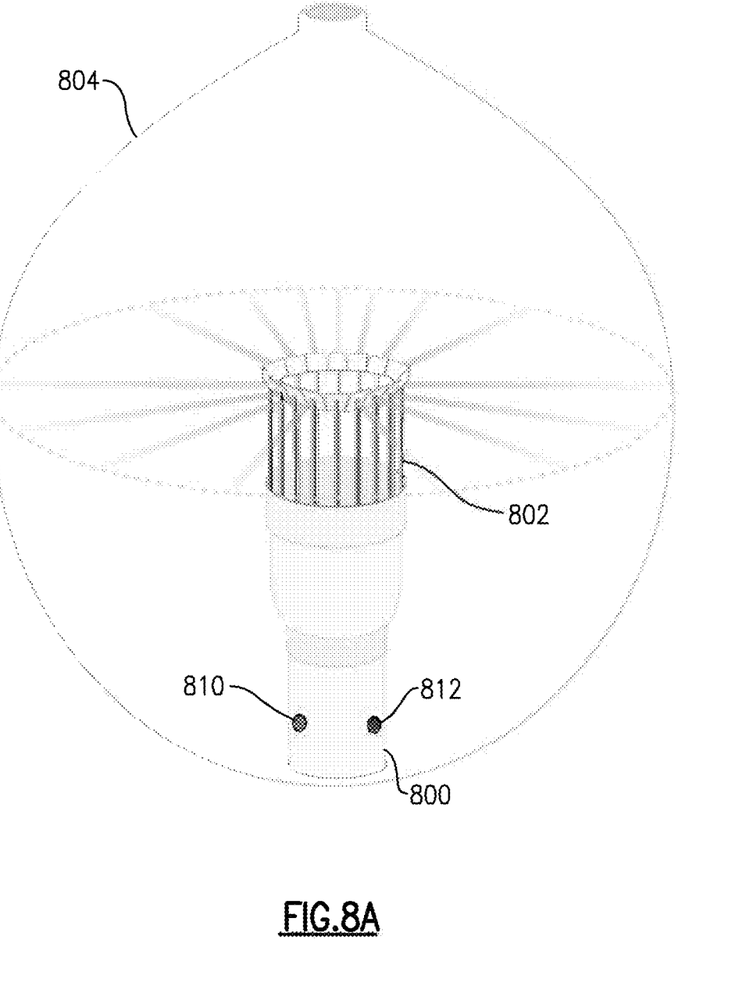
FIG. 8A illustrates an ablation catheter including an electrode using laser energy, according to certain embodiments.

FIG. 8A illustrates an ablation catheter 800 and a laser energy delivery system 802, according to certain embodiments. Ablation using laser energy is advantageously faster than ablation using RF energy. The ablation catheter 800 and laser energy delivery system 802 are used in conjunction with the angionavigation catheter 100 to ablate arrhythmogenic tissue. The ablation catheter 800 is deployed through the central lumen of the angionavigation catheter 100.

After placement of the catheter 100 under angionavigation, in, for example, the left pulmonary vein, the laser catheter 800 is deployed. The laser delivery system 802, in an embodiment, is inside a clear balloon 804 with an inflow port 810 for inflow of cold air, water, or the like, and an outflow port 812 for outflow of warm air, water, or the like, to constantly keep the left pulmonary vein antrum cool during the ablation, and has the function of stopping the blood flow into the left atrium during the ablation. A laser delivers laser power of approximately 4 to approximately 20 watts via fiber optic to an approximately 45° mirror reflecting on to the left pulmonary vein antrum. The laser energy reflects from the mirror at an approximately 90° angle relative to the longitudinal axis of the fiber optic and projects onto the tissue to be ablated. In an embodiment, the fiber optic comprises approximately 16 fibers.

Figure 8B:
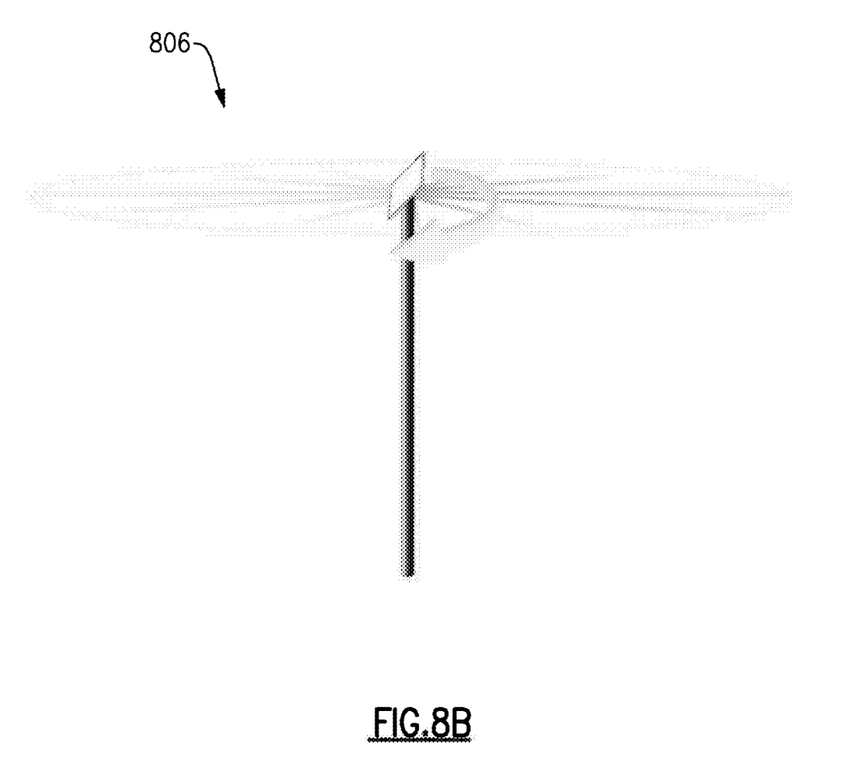
FIG. 8B illustrates another embodiment of an ablation electrode.

FIG. 8B illustrates another embodiment of an ablation electrode 806. According to certain embodiments, the laser energy is delivered to an approximately 45° rotating mirror via a single fiber that ablates the circumference of the antrum in seconds.

Figure 9:
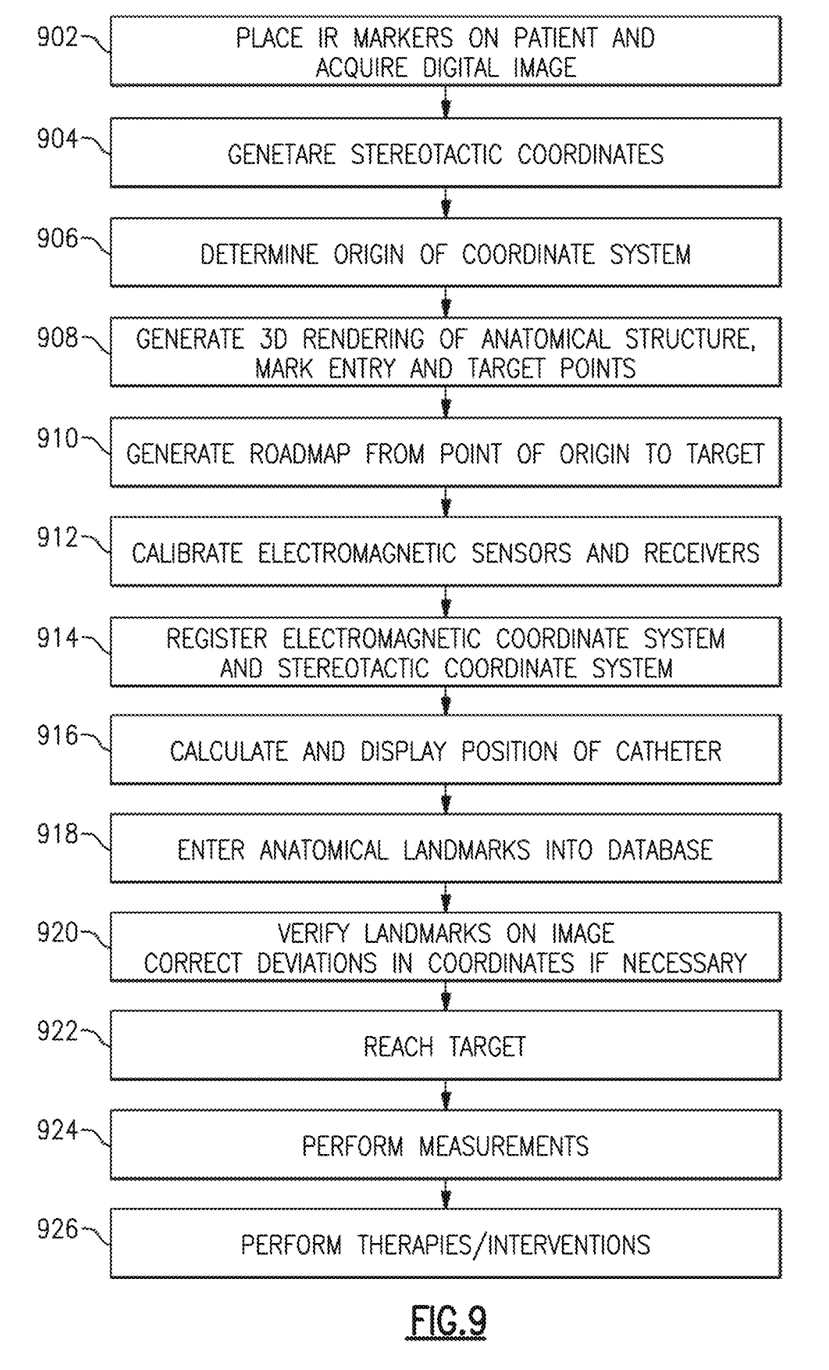
FIG. 9 is a schematic block diagram of a method of utilizing an angionavigation system, according to certain embodiments.

FIG. 9 is a schematic block diagram of a method 900 of utilizing an angionavigation system, according to certain embodiments. Beginning at block 902, the patient 512 is placed onto the couch 504 in the angionavigation suite 500. The IR markers 510 are placed on the patient's skin and the MRA digital image of the patient 512 is loaded. The MRA is an image taken without ionizing or iodinated agents. In an embodiment, the high resolution MRA is taken previously of the patient. In other embodiments, if MRA is not available, a CTA digital image is used. The CTA ionizing radiation dose is significantly less than conventional angiography.

At block 904, the computer 514 receives the digital image. The computer 514 executing the navigational module 400 generates stereotactic coordinates based at least in part on the locations of the IR markers 510 in the digital image.

At block 906, the location chosen to be the origin of the stereotactic coordinate system is marked on the MRA image, as well as the target for the intervention or therapy. In an embodiment, the catheter entry point is the origin.

At block 908, the method 900 generates a 3D rendering of the anatomical structure, such as the cardiovascular system, with the entry and target points marked.

At block 910, the computer 514 executing the navigational module 400 generates a roadmap from the point of origin to the target and displays the roadmap onto the 3D rendering or roadmap image 300. In an embodiment, the roadmap displays suggested veins and arteries to snake the catheter 100 through to reach the target tissue.

At block 912, the electromagnetic sensors 116 and the RF receivers 508 in the angionavigation suite 500 are calibrated.

At block 914, the user places the catheter 100 at the entry point in the patient 512 and the electromagnetic coordinate system is zeroed. Thus, the origin of the electromagnetic coordinate system and the origin of the stereotactic coordinate system are registered/fused.

At block 916, the user snakes the catheter 100 along the roadmap within the roadmap image 300 displayed on the monitor 520. The RF receivers 508 interrogate the tracking sensors 116 to obtain positional information and triangulate the positional information to determine the position of the catheter tip. The monitor also displays the catheter tip on the roadmap image 300.

At block 918, through direct visualization of the cardiovascular system, desired anatomical landmarks are entered into a database stored in memory 516. Each anatomical landmark is entered into the computer to make the position of the catheter 100 relative to the vascular anatomy accurate with high precision. As the catheter tip comes close to a noted landmark, the program 400 notifies the user of the distance between the tip and the noted landmark.

At block 920, the landmarks on the MRA image are verified and co-registered with the images on the roadmap image 300. Any deviations are corrected and reregistered.

At block 922, in an embodiment, the navigational software 400 directs the user to steer the catheter in a suggest direction in order to more directly and efficiently reach the target.

At block 924, the catheter 100 reaches the target. The angiovision hardware and software display 2D or 3D video images of the target from the camera and associated fiber optic bundle(s) 112. In an embodiment, the extent of the vascular plaques or aneurysm may be displayed on a computer screen via fiber optics and a camera connected via a connector, such as a USB, USB2, or the like, to a laptop computer screen.

At block 926, the user performs desired measurements, such as but not limited to blood flow rate, temperature, pressure, volume, electrogram, optical spectroscopy of the ablated tissue, and the like, using the sensors, such as but not limited to the ultrasound transducer 104, the electrogram and pacing sensors 106, and the like.

At block 928, the user performs angiotherapeutics, such as but not limited to, ablation, angioplasty, insert a stent, dilation, and the like. In an embodiment, the procedure can be recorded in a laptop or other computer system for instant replay or archived for future analysis.

While the systems and methods for angiovision, angionavigation and angiotherapeutics described herein with respect to the cardiac system and the heart, a skilled artisan will also appreciate in light of this disclosure that other embodiments of angiovision, angionavigation and angiotherapeutics can be performed on other systems, muscles, and organs, including, but not limited to the liver, lungs, kidneys, pelvis, pancreas, pleura, brain, uterus, cervix, spine, esophagus, stomach, small bowl, colon and rectum.

The computer 514 comprises, by way of example, processors, program logic, or other substrate configurations representing data and instructions, which operate as described herein. In other embodiments, the processors can comprise controller circuitry, processor circuitry, processors, general-purpose single-chip or multi-chip microprocessors, digital signal processors, embedded microprocessors, microcontrollers and the like. The memory 516 can comprise one or more logical and/or physical data storage systems for storing data and applications used by the computer 514. The memory 516 comprises, for example, RAM, ROM, EPROM, EEPROM, and the like.

In one embodiment, the program logic may advantageously be implemented as one or more modules 400. The modules may advantageously be configured to execute on one or more processors. The modules may comprise, but are not limited to, any of the following: software or hardware components such as software object-oriented software components, class components and task components, processes methods, functions, attributes, procedures, subroutines, segments of program code, drivers, firmware, microcode, circuitry, data, databases, data structures, tables, arrays, or variables.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The words "coupled" or connected", as generally used herein, refer to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

Moreover, conditional language used herein, such as, among others, "can," "could," "might," "may," "e.g.," "for example," "such as" and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The above detailed description of certain embodiments is not intended to be exhaustive or to limit the invention to the precise form disclosed above. While specific embodiments of, and examples for, the invention are described above for illustrative purposes, various equivalent modifications are possible within the scope of the invention, as those ordinary skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times.

The teachings of the invention provided herein can be applied to other systems, not necessarily the systems described above. The elements and acts of the various embodiments described above can be combined to provide further embodiments.

While certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

What is claimed is:

1. A method to navigate within body structures, comprising:
    creating a digital image of a patient and at least one marker placed external to the patient, the digital image including image information obtained from an image of the at least one marker and from an image of a vascular system of the patient that are acquired by an imaging system that does not use ionizing radiation and iodinated agents, the digital image further including image information from images of the at least one marker captured by two cameras that are positioned at different positions with respect to the patient;
    generating stereotactic coordinates in a stereotactic coordinate system based at least in part on locations of the at least one marker detected by the imaging system and the two cameras;
    generating from the digital image a 3D rendering of the vascular system in stereotactic space, the 3D rendering including indications of an entry point of a catheter and a target, the catheter including at least one electromagnetic sensor associated with an electromagnetic coordinate system;
    co-registering the electromagnetic and the stereotactic coordinate systems; and
    fusing a position associated with the catheter onto the 3D rendering, the position obtained from a tracking system configured to track the at least one electromagnetic sensor.

2. The method of claim 1 further comprising displaying the 3D rendering.

3. The method of claim 2 wherein the displayed 3D rendering includes indications for positions of the catheter, the entry point, and the target.

4. The method of claim 1 wherein the imaging system includes a magnetic resonance angiography system.

5. The method of claim 1 wherein the at least one marker comprises at least one infrared marker and each of the two cameras comprises an infrared camera.

6. The method of claim 1 wherein the locations of the at least one marker detected by the imaging system and the two cameras provide registration information for the stereotactic coordinate system.

7. The method of claim 1 wherein the catheter further includes a fiber optic bundle and a first camera different from the two cameras that is in communication with the fiber optic bundle.

8. The method of claim 1 wherein the catheter provides an angioscopic view of the target.

9. The method of claim 1 further comprising generating a roadmap from the entry point to the target on the 3D rendering.

10. The method of claim 9 wherein the displayed 3D rendering includes the roadmap and indications for positions of the catheter, the entry point, and the target.

11. The method of claim 1 wherein co-registering the electromagnetic and the stereotactic coordinate systems fuses positional information of the at least one electromagnetic sensor with the 3D rendering.

12. The method of claim 1 wherein the tracking system comprises an in-room global positioning system.

13. The method of claim 1 wherein the position associated with the catheter comprises longitudinal, lateral, anterior-posterior, pitch, roll, and yaw locations of the catheter.

14. The method of claim 1 further comprising providing the 3D rendering for use in image guided cytotoxic drug delivery or radioactive seed implants into tumors.

15. An ionizing radiation-free angionavigation system comprising:
    a first preoperative imaging system comprising at least two cameras, each camera configured to capture an image of at least one external stereotactic fiduciary marker from a different position with respect to a patient;
    a second preoperative imaging system configured to capture a digital image of a vascular system of the patient and the at least one external stereotactic fiduciary marker utilizing non-ionizing radiation and non-iodinated agents;
    a computer image system in communication with the first and second preoperative imaging systems to create stereotactic coordinates of the at least one external stereotactic fiduciary marker using the digital image, the computer image system configured to generate, based on image information from the first preoperative imaging system and from the second preoperative imaging system, a 3D rendering in stereotactic space of the vascular system, the 3D rendering marking a point of entry and a target using a stereotactic coordinate system; and a tracking system in communication with the computer image system and configured to provide location information of at least one electromagnetic sensor associated with a catheter, the tracking system providing the location information using an electromagnetic coordinate system, the computer image system further configured to register the electromagnetic coordinate system with the stereotactic coordinate system to fuse the location information with the 3D rendering.

16. The system of claim 15 wherein images captured by the first preoperative imaging system of the at least one external stereotactic fiduciary marker are configured to provide registration locations for the stereotactic coordinate system.

17. The system of claim 16 wherein an origin of the stereotactic coordinate system is defined as the point of entry.

18. The system of claim 15 wherein the electromagnetic coordinate system is independent of the stereotactic coordinate system.

19. The system of claim 15 further comprising the catheter.

20. The system of claim 15 wherein the 3D rendering is used to navigate the catheter from the point of entry to the target.

21. The system of claim 20 wherein the catheter further comprises a camera operationally connected to a fiber optic bundle to provide an angioscopic view of tissue during the navigation and therapeutic interventions.

22. The system of claim 20 wherein the 3D rendering is used in image guided stent placement, ventricular shunt evaluations, ablation of arrhythmogenic tissue or ablation of tumors.

* * * * *